(12) United States Patent
Holtzman

(10) Patent No.: US 9,913,499 B1
(45) Date of Patent: Mar. 13, 2018

(54) INFLATABLE PADS BIKER SHORTS

(71) Applicant: Larry Holtzman, Dallas, TX (US)

(72) Inventor: Larry Holtzman, Dallas, TX (US)

(*) Notice: Subject to any disclaimer, the term of this patent is extended or adjusted under 35 U.S.C. 154(b) by 0 days.

(21) Appl. No.: 15/483,296

(22) Filed: Apr. 10, 2017

Related U.S. Application Data

(63) Continuation of application No. 15/016,571, filed on Feb. 5, 2016, now abandoned.

(51) Int. Cl.
*A41D 1/08* (2006.01)
*A41D 13/015* (2006.01)
*F04B 9/14* (2006.01)
*F04B 17/03* (2006.01)
*F04B 43/02* (2006.01)

(52) U.S. Cl.
CPC ......... *A41D 1/084* (2013.01); *A41D 13/0155* (2013.01); *F04B 9/14* (2013.01); *F04B 17/03* (2013.01); *F04B 43/02* (2013.01); *A41D 1/08* (2013.01)

(58) Field of Classification Search
CPC . A41D 1/06; A41D 1/08; A41D 13/02; A41D 13/018; A63B 71/1216
See application file for complete search history.

(56) References Cited

U.S. PATENT DOCUMENTS

| | | | | |
|---|---|---|---|---|
| 1,468,072 A | * | 9/1923 | Ogle | A47C 7/021 128/889 |
| 5,086,514 A | * | 2/1992 | Ross | A41D 13/0155 128/DIG. 20 |
| 5,271,101 A | * | 12/1993 | Speth | A41D 1/084 2/214 |
| 5,500,952 A | * | 3/1996 | Keyes | A41D 13/018 2/465 |
| 7,017,195 B2 | * | 3/2006 | Buckman | A41D 13/018 2/455 |
| 7,739,754 B2 | * | 6/2010 | Garneau | A41D 1/084 2/215 |
| 7,823,219 B2 | * | 11/2010 | Freund | A61F 13/143 2/69 |
| 8,095,994 B2 | * | 1/2012 | Natonson | A61H 9/0078 2/102 |
| 2014/0250567 A1 | * | 9/2014 | Kaviani | A41D 1/084 2/228 |

* cited by examiner

*Primary Examiner* — Tejash Patel
(74) *Attorney, Agent, or Firm* — Richard G. Eldredge; Eldredge Law Firm

(57) ABSTRACT

A bicycle shorts system includes a bicycle shorts having a waist section configured to fit around a waist area of the user; a first leg section and a second leg section integral with and secured to the waist section; and a padded area having a material extending from the first leg section to the second leg section, the padded area forming a cavity. The system further includes a liquid filling assembly having a first liquid chamber carried by the first leg section; and a second liquid chamber carried by the second leg section. The method includes filling the first liquid chamber and the second liquid chamber.

8 Claims, 5 Drawing Sheets

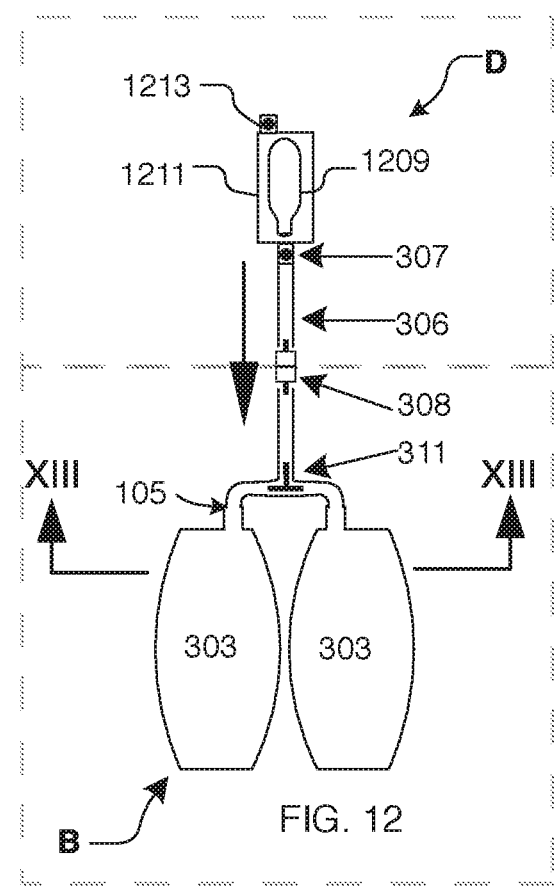

INFLATABLE PADS BIKER SHORTS

BACKGROUND

1. Field of Invention

The present invention relates generally to bicycling shorts and more specifically, to adjustable Inflatable pads in bicycling shorts.

2. Description of Related Art

Bicycling shorts are well known in the art as an effective means to reduce the pain and soreness due to pressure on nerves around the sit bone and perineal area of the buttocks and crotch from the seat or saddle of the bicycle after long and bumpy rides. FIG. 1 depicts a common known pair of bicycling shorts 101 having a waist section 102 along with two integral leg sections 103 and 104. Disposed between the two leg sections 103 and 104 are pads 105 configured to provide extra cushioning between the buttocks and crotch of the cyclist and the bicycle seat.

One disadvantage of the pads 105 is its limited use. Specifically, the pads are not adjustable. With pads that aren't adjustable, pressure on the nerves around the sit bones and perineal area become sensitive and painful especially after lengthy periods of time riding. Imagine sitting on a padded chair for hours which was comfortable at first but as time goes on, becomes very painful and uncomfortable until repositioning oneself is necessary to relieve this discomfort. With the ability to control the pads thickness and conformity, the pressure on the nerves is relieved if not eliminated. For example, a rider may wish to start his/her ride off with a minimal amount of padding and be able to add additional cushioning as needed when the saddle becomes uncomfortable as needed. Pads 105 do not accommodate for these desires.

Although great strides have been made in the area of bicycling shorts, many shortcomings still remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

FIG. 3 is a disassembled view of the bicycle shorts of FIG. 2; It is important to note that dashed boxes separate the two different inflation systems A top and B bottom. To make things easy to remember "A" stands for "air" which is where the air originates from, and "B" stands for "Bladder" where the air ends up accumulating in.

FIG. 12 is a frontal view of an inflation system FIG D in accordance with an alternative embodiments of the present application.

Figure 1:
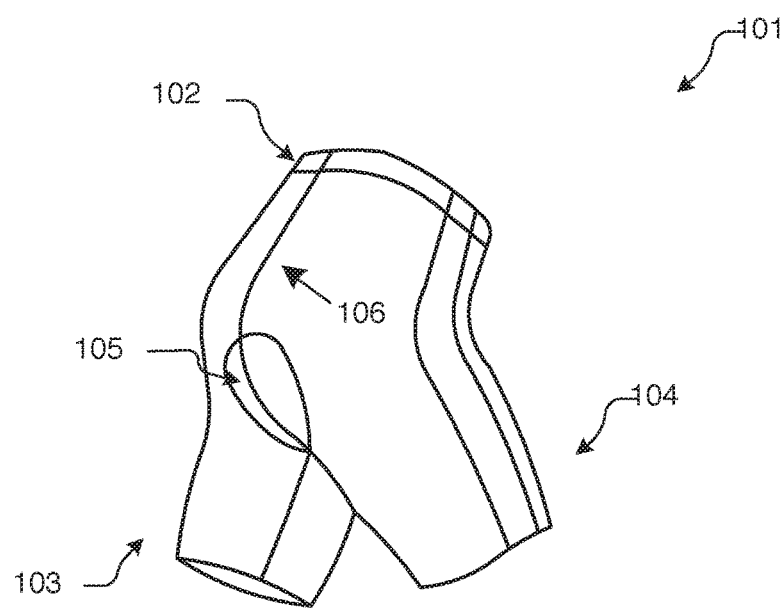
FIG. 1 is an oblique rear view of a conventional pair of bicycle shorts.

While the system and method of use of the present application is susceptible to various modifications and alternative forms, specified embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional bicycle shorts. Specifically, the system and method of the present application provides rapid and effective means to inflate/fill the containment reservoirs or bladders carried within the thickness of the bicycle shorts, which in turn allows selective adjustment of the cushioning between the cyclist and the bicycle's saddle. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components and parts (such as Air supply 309; air release valve 307; hoses 306, couplings 308; air containment reservoirs or bladders and different fabrics. with features and methods (such as Control of air supply 1209, 809 & 309 & 307; detachment device 108 of the air supply A, C & D from the air containment reservoirs or bladders 303; placement or stem 305 where the hose attaches to the air containment reservoirs or bladders; configuration of the air containment reservoirs or bladders 303; and channels or tunnels stitched into the fabric 401; of the bicycle shorts specifically the back 105 and waist 102 seams to conceal the hoses) of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
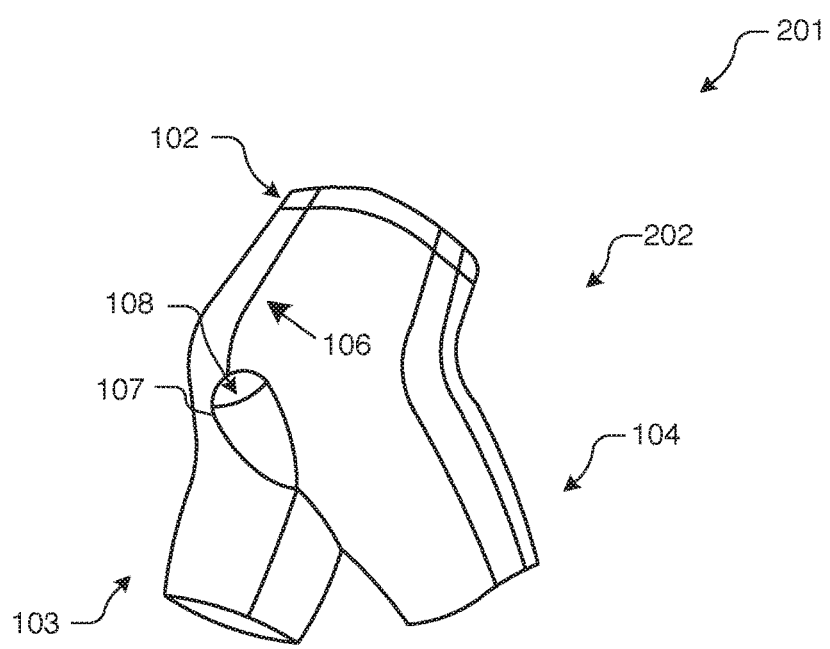
FIG. 2 is an oblique rear view of a pair of bicycle shorts in accordance with a preferred embodiment of the present application.
Figure 3:
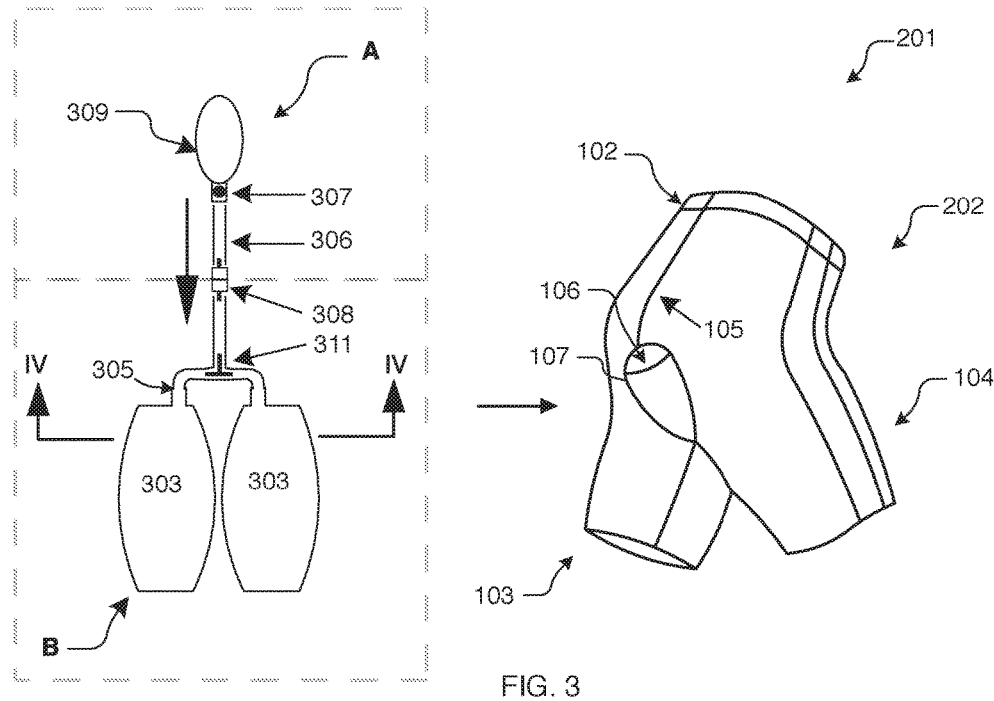

Referring now to the drawings wherein like reference characters identify corresponding or similar elements throughout the several views, FIG. 2 and FIG. 3 depict oblique views of a bicycle shorts system 201 in accordance with a preferred embodiment of the present application. It will be appreciated that system 201 overcomes one of more of the above-listed problems commonly associated with the conventional bicycle shorts shown in FIG. 1.

In the contemplated embodiment, system 201 includes bicycle shorts 202 and an operable associated inflation system having components A & B. Bicycle shorts 202 includes a waist section 102 joined together with two leg sections 103 & 104. Disposed between leg sections 103 & 104 and partially joining a portion of waist section 102, is a padding area 105 that forms a cavity 106 with material 107 configured to receive one or more of the inflation systems, e.g., system with components A and B discussed herein.

One of the unique features believed characteristic of the present application is the use of an inflation system to selectively adjust the cushioning between the cyclist and the seat of the bicycle (not shown). To achieve this features, it is contemplated using an inflation system such as inflation system B in FIGS. 3 & 4 having air containment reservoirs or bladders 303 that fit within the cavity 106. It should be noted that the cavity 106 can be placed on either inside of the bicycle shorts (inner or outer) and then later permanently sealed or left open and temporarily sealed thus being able to reopen the cavity 106 using a closing device such as a zipper or Velcro® strips after placement of air containment reservoirs or bladders 303 therein. (Refer to FIG. 4 for embodiment illustrating inner placement of pads).

Figure 5:
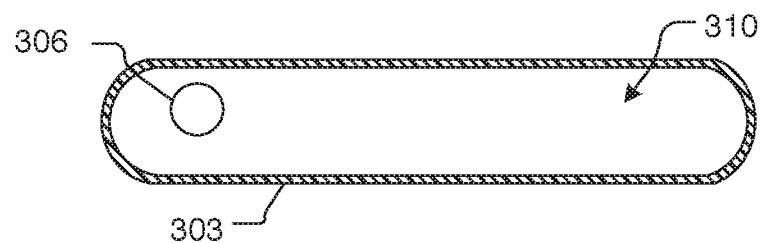
FIG. 5 is a cross-sectional view of the air containment reservoirs or bladders of the biker shorts of FIG. 3 taken at IV-IV.

To reach the internal air chamber 310 (as shown in FIG. 5) in the air containment reservoir or bladder 303, a hose 306 is in gaseous communication therewith. An air pressure release valve 307 is used to regulate air flow through hoses 306, coupling 308 and stem 305, configured to engage with an inflation device B. In the exemplary embodiment, inflation device A is an elastic hand pump (Standard Flat Bottom Bulb 309 with plastic push-button air release valve and metal back valve 307); however, it is also contemplated using alternative inflation devices such as a battery powered 811 motorized system (see. e.g., C) or compressed air (see, e.g., D). Before the preferred embodiment can be used the rider would secure the inflation device A, C or D using coupling 308 resulting in opening up a clear air passage after being attached to the air containment reservoirs or bladders, then manipulating air into the bladders. A "T" connector 311 and hoses 306 enable the air to pass into the air containment reservoirs or bladders 303. Thereafter the pressure release valve 307 can be manipulated to regulate the amount of pressure going to the air containment reservoirs or bladders 303 which in turn changes the cushion effect of the pads in the bicycle shorts and softens the impact between the cyclist and the bicycle's saddle.

It will be appreciated that the preferred embodiment includes the features of filing the internal air containment reservoir or bladder chamber 310 with gas e.g., air; however, it is also contemplated using a liquid in lieu of gas. In this embodiment, the liquid would fill the containment reservoir or bladder chamber 310 via a pump in communication with a liquid supply (not shown) and could be released with one or more of the valve systems discussed herein.

In order to prevent the air containment reservoirs or bladders 303 from getting liquid into it, it is necessary to have a closed air tight system B. To accomplish this a special coupling 308 is needed. The reason for coupling 308 is so that the air inflation system A, C or D can be disconnected from the air containment reservoirs or bladders 303 resulting in a closed air tight system B when washing the shorts, thus keeping fluid from getting into the air containment reservoirs or bladders when submerged. Coupling 308 is a two piece connector with its barbed ends each attached to a hose 306 at one end and having a twist locking mechanism at the other. When the coupling is separated from its other half, a built in valve in the connector attached to the inflation system B seals the air containment reservoirs or bladders 303 shut when uncoupled. The other connector attached to the air inflation system A, C or D has a straight thru air passage design with no valve and would be connected to the hose that feeds air from the pump 809, 1209 or 309 with pressure release valve 307. Before being able to feed air into the air containment reservoirs or bladders 303, the cyclist would twist and connect the two halves of the coupling 308 (In-line straight thru SMC02MBLK with barb and In-line shutoff SMCD02MBLK with barb) securing the inflation device A, C or D to the inflation system B. By depressing the hand pump 309, button 1213 or switch 808 air can be forced into the containment reservoirs or bladders 303. The pressure release valve 307 can then be manipulated to regulate the air pressure in the air containment reservoirs or bladders 303, which in turn changes the cushioning effect of the pads by inflating and deflating them.

Figure 4:
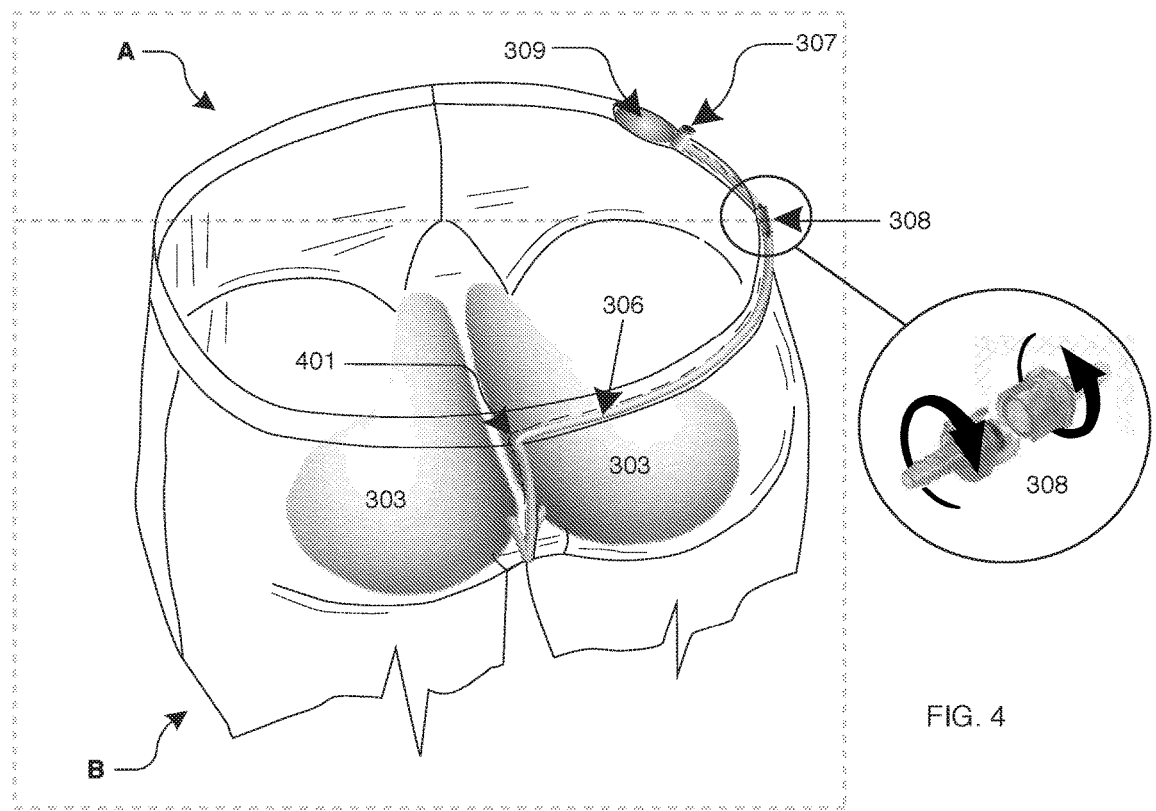
FIG. 4 is a top view of the bicycle shorts of FIGS. 2 & 3 with the air containment reservoirs or bladders shown on the inside of the bicycle shorts with attached tubing or hose including a pump, pressure release valve, couplings and connectors described later in more detail.

FIG. 4. Is a top 3D view of all the components in FIG. 3 seen with the air containment reservoir or bladders located inside the bicycle shorts. It is also worth noting that A, C or D and pressure release valve 307 are located in the waist band 102 of the shorts 202. Stitching 401 creates a channel or tunnel in the fabric of the shorts for the tubing/hose to run through, making the bicycle shorts appearance more visually aesthetic.

Figure 6:
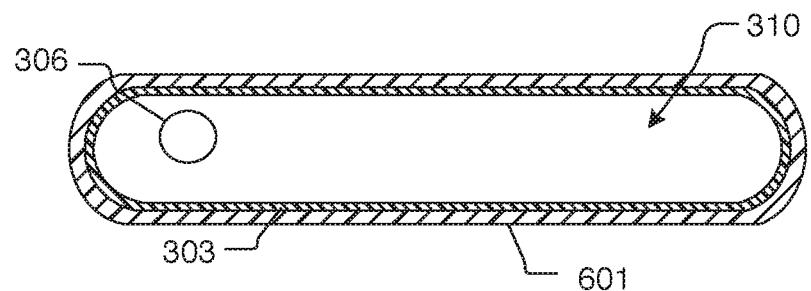
FIG. 6 is a cross-sectional view of the air containment reservoir or bladder FIG. 5 in accordance with an alternative embodiment of the present application; taken at IV-IV.

In FIG. 6, is a cross-sectional view of a bladder shown in accordance with an alternative embodiment of the present application. It will be appreciated that it is also contemplated utilizing a gel or foam sheeted material 601 firmly attached to the outer periphery of the bladder 303. This feature enhances the cushioning of system "B" between the rider and the seat of the bicycle.

Figure 7:
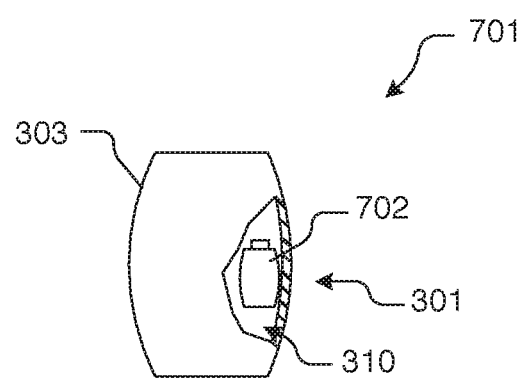
FIG. 7 is a front view of an inflation system in accordance with an alternative embodiment of the present application.
Figure 8:
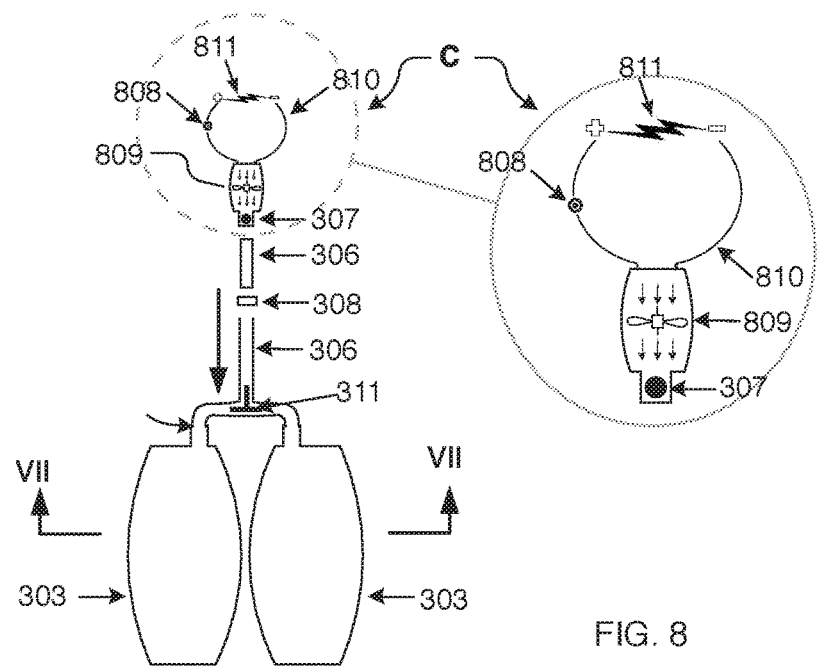
FIG. 8 is a front view of a motorized inflation system C in accordance with an alternative embodiment of the present application.

Referring now to FIGS. 7 & 8: FIG. 7 is a partial cutout view of an inflation system B shown in accordance with an alternative embodiment of the present application. System 701 includes a bladder 303 that forms a gas chamber 310. In this embodiment, the self-inflation device 702, e.g., an electric 811 pump as illustrated in FIG. 8 is positioned within the air chamber 310. This feature pro-vides advantages such as reducing the space required to inflate the bladder with the self-inflation system C being carried within the air containment reservoirs or bladders. Inflation system C being a motorized fan 809 engaged with a switch 808 connected with wires 810 from an electric supply 811 and a pressure release valve 307.

Figure 9:
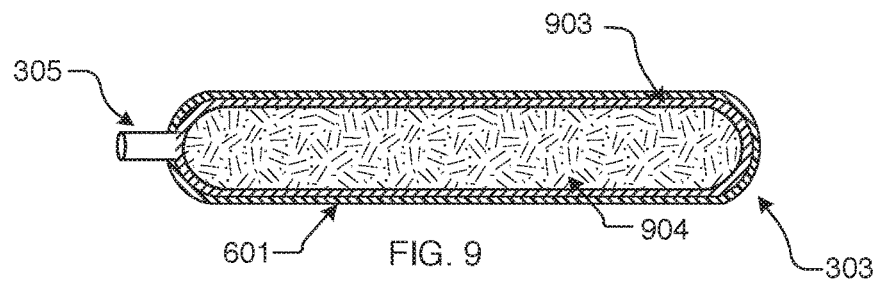
FIG. 9 is a cross-sectional view of the air containment reservoirs or bladders taken at XIII-XIII of FIG. 8.

In FIG. 9, a cross-sectional of an inflation system B is shown in accordance with an alternative embodiment of the present application. In this embodiment, a liner 903 is used to self-inflate the air containment reservoirs or bladders 303. Like the previous inflation systems, inflation system in FIG. 9 includes a bladder 303 but instead of an air chamber 310 a foam or gel core 904 using a stem or connection 305 is in gaseous communication with the liner 903.

Figure 10:
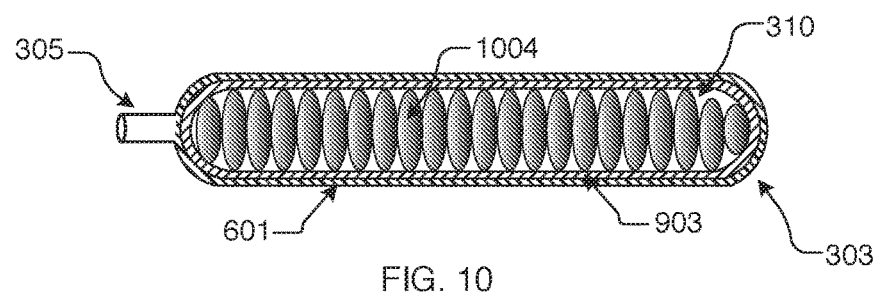
FIG. 10 is a cross-sectional view of the air containment reservoirs or bladders taken at XIII-XIII of FIG. 8.

FIG. 10 is a cross-sectional view of an inflation system B shown in accordance with an alternative embodiment of the present application. In this embodiment, an inflation device A, C or D combined with a pump 109, 809 or 1209 and pressure release valve 307 is used to self-inflate a liner 903 that is in gaseous communication with a stem or connection 305. Instead of a core 904 it is contemplated to use air cells 1004 would be individual air cell chamber that are sealed and air tight. This would aid in configuring to the contour of the riders behind and increase comfort.

Figure 11:
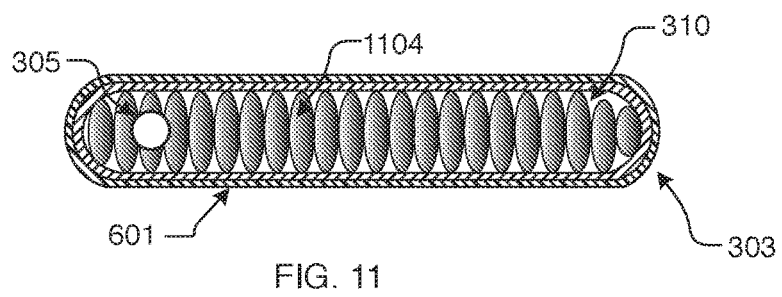
FIG. 11 is a cross-sectional view of the air containment reservoirs or bladders taken at XIII-XIII of FIG. 8.

FIG. 11 is a cross-sectional view of an inflation system B shown in accordance with an alternative embodiment of the present application. In this instance there is no liner 903. In air chamber 310 air cells 1104 are in gaseous communication with one another and with a stem 305 and hose 306. The air containment reservoirs or bladders would be made of a web of air pockets or cells in the cavity 310 and would inflate using an air supply shown in inflation system A, C or D.

It will be appreciated that alternative embodiments could use compressed air in lieu of a hand or electric 811 pump. This feature is shown in FIG. 12, specifically, a system D includes air containment reservoirs or bladders 303 with a stem or connection 105, a coupling 108 as seen in FIGS. 3 & 4 configured to engage with inflation system B and pressure release valve 107. The system 1102 includes a compressed air cylinder 1109 carried within a housing 1011 and operably associated with a button 1113 or the like for releasing the air from the cylinder into air containment reservoirs or bladders and using the pressure release valve 107 to adjust the size of air containment reservoirs or bladders 303. A hose 106 provides air passage from system C to the inflation system B of the air containment reservoirs or bladders 303 once the two systems are joined together using coupling 108.

It will be appreciated that one or more of the features discussed with each system could be incorporated with each other although depicted as separate systems.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A bicycle shorts system, comprising:
   a bicycle shorts having:
      a waist section configured to fit around a waist area of a user;
      a first leg section and a second leg section integral with and secured to the waist section; and
      a padded area forming a seat section and having a material extending from the first leg section to the second leg section, the padded area forming a cavity, the seat section having a right side and a left side; and
   a liquid filling assembly, having:
      a first liquid chamber carried by the first leg section and making up the right side of the seat section; and
      a second liquid chamber carried by the second leg section and making up the right half of the seat section;
      a tube in fluidic communication with the first liquid chamber and the second liquid chamber;
      a coupling attached to the tube and secured to the waist section of the bicycle shorts;
      a pump disposed within the waist section and configured to be secured to the coupling; and
      a liquid supply in communication with the pump and configured to provide a volume of liquid to be moved via the pump;
   wherein the tube passes through the cavity of the padded area of the seat section and extends around a portion of a periphery of the waist section to the coupling and to the pump;
   wherein the pump is in fluidic communication with the tube;
   wherein the first liquid chamber and the second liquid chamber are disposed within the thickness of the respective first leg section and the second leg section of the seat section; and
   wherein the liquid filling assembly is configured to fill with liquid from the liquid supply during use, which in turn creates a greater thickness in the first leg section and the second leg section of the seat section.

2. The system of claim 1, wherein the pump is a hand pump.

3. The system of claim 1, wherein the pump is a mechanical liquid pump.

4. The system of claim 3, the mechanical liquid pump further comprising:
   a switch; and
   a battery;
   wherein the switch is configured to activate the pump; and
   wherein the battery is configured to provide electrical energy to the pump.

5. The system of claim 1, wherein the first liquid chamber and the second liquid chamber form a single liquid bladder in communication with a tube.

6. A method to fill bicycle shorts, comprising:
   providing the system of claim 1;
   filling the first liquid chamber and the second liquid chamber.

7. The method of claim 6, further comprising:
   directing liquid into the first chamber and the second chamber with a hand pump.

8. The method of claim 6, further comprising:
   directing liquid into the first chamber and the second chamber with an electric pump.

* * * * *